United States Patent [19]

Peters

[11] Patent Number: 5,074,454

[45] Date of Patent: Dec. 24, 1991

[54] SURGICAL STAPLER

[76] Inventor: Ronald L. Peters, 5029 Blackhawk Dr., Danville, Calif.

[21] Appl. No.: 533,073

[22] Filed: Jun. 4, 1990

[51] Int. Cl.$^5$ ............................................. A61B 17/072
[52] U.S. Cl. ........................................ 227/178; 227/19
[58] Field of Search ................. 227/175, 178, 180, 19, 227/21, 30

[56] References Cited

U.S. PATENT DOCUMENTS

| | | |
|---|---|---|
| 3,490,675 | 1/1970 | Green et al. |
| 3,494,533 | 2/1970 | Green et al. |
| 3,499,591 | 3/1970 | Green ................................... 227/76 |
| 4,520,817 | 6/1985 | Green ................................... 227/19 |
| 4,605,001 | 8/1986 | Rothfuss et al. ..................... 227/178 |
| 4,608,981 | 9/1986 | Rothfuss et al. ..................... 227/180 |
| 4,633,861 | 6/1987 | Chow et al. ........................... 227/19 |
| 4,633,874 | 6/1987 | Chow et al. ........................... 227/19 |
| 4,991,764 | 2/1991 | Mericle ................................ 227/178 |

*Primary Examiner*—Mark Rosenbaum
*Assistant Examiner*—Rinaldi Rada

*Attorney, Agent, or Firm*—Harris Zimmerman

[57] ABSTRACT

A surgical instrument for implanting one or more rows of staples in living tissue has a pair of juxtaposed beam members with forward portions that jointly define a thin gap in which the tissue may be received and clamped. A latch couples the beam members together at a location behind the tissue gap. Operation of a first actuator forces staples out of one of the beam members and into the tissue, the other beam member having indentations shaped to close the staples. A tensioner flexes the beam members to create internal stresses which resist spreading of the beam member tips in response to load forces that are exerted on the members by clamped tissue and the stapling operation. This assures that the gap has a uniform width along its length and thus assures that the successive staples are each formed into an optimum configuration. The tensioner is actuated prior to and independently of operation of the first actuator and thus does not require exertion of additional effort nor interfere with tactile feedback to the surgeon during the stapling operation.

18 Claims, 8 Drawing Sheets

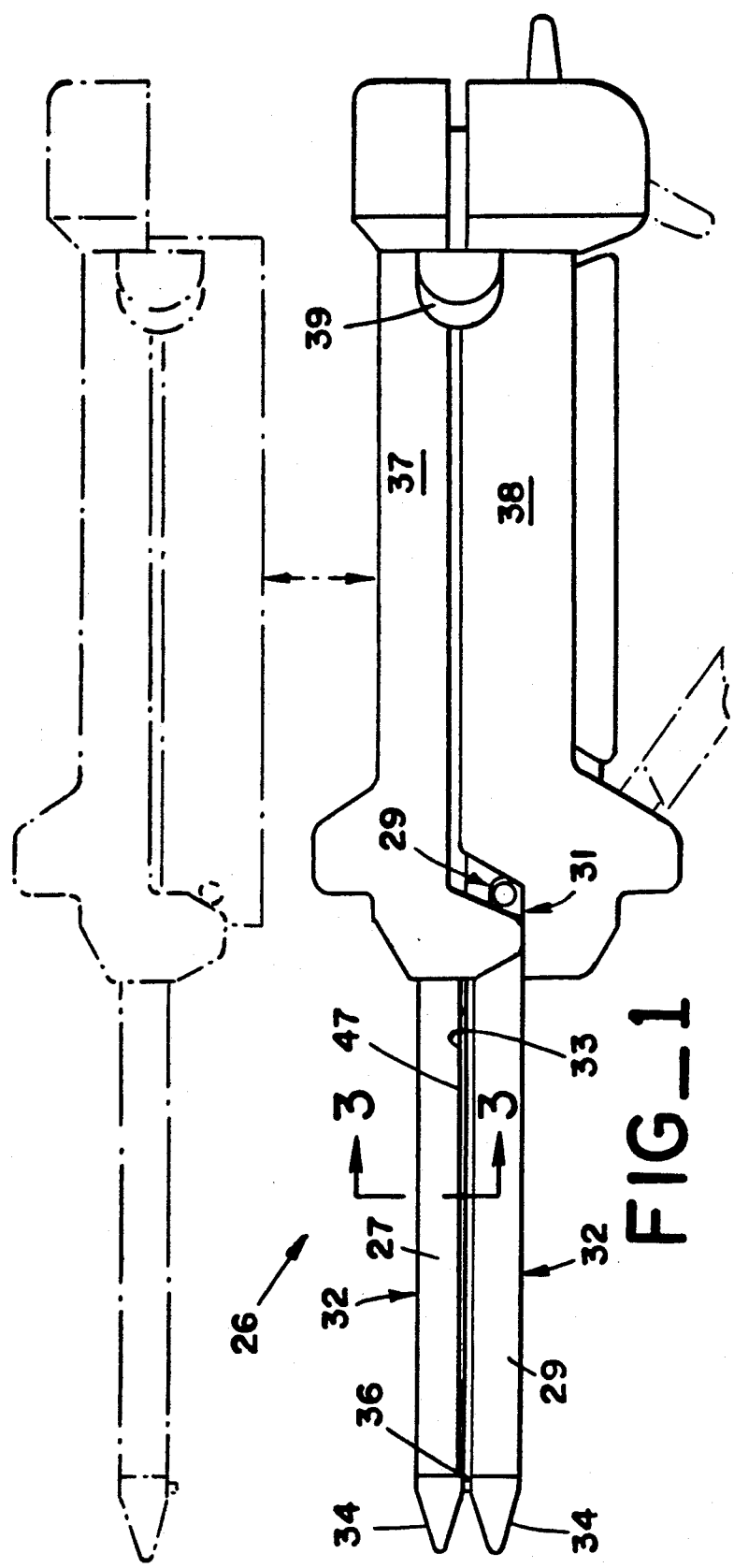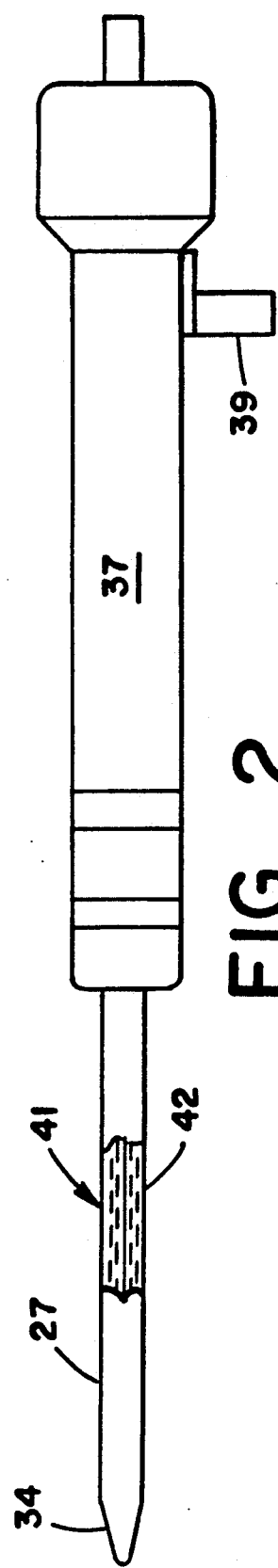

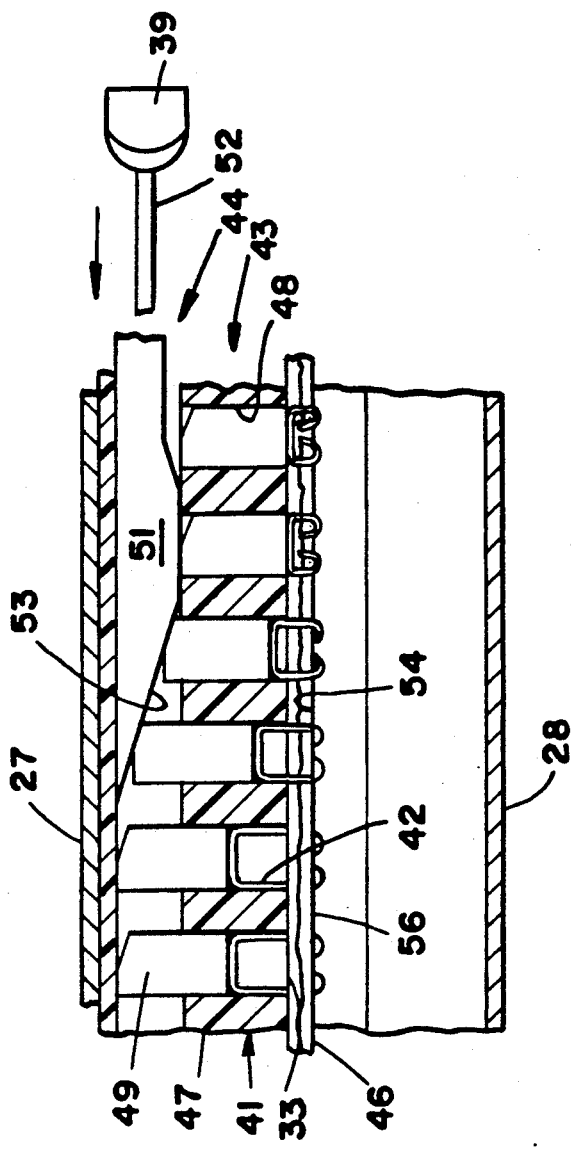
FIG_4
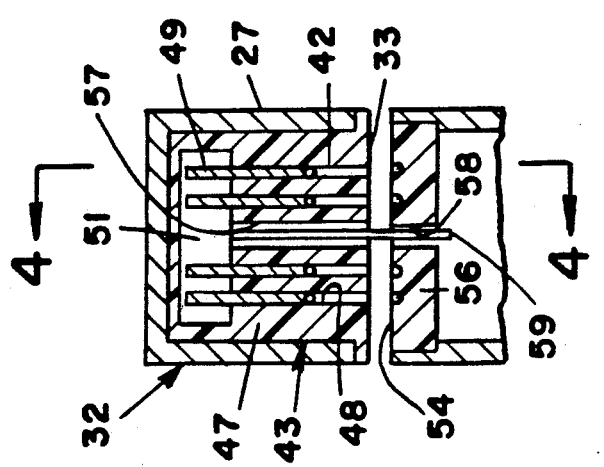
FIG_5
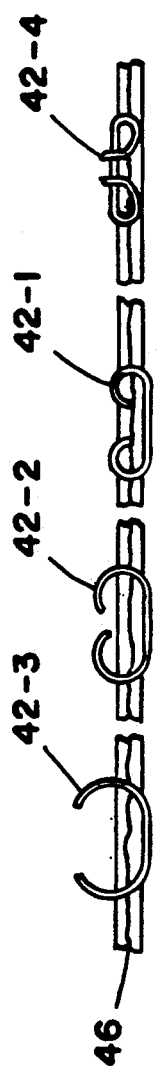
FIG_3

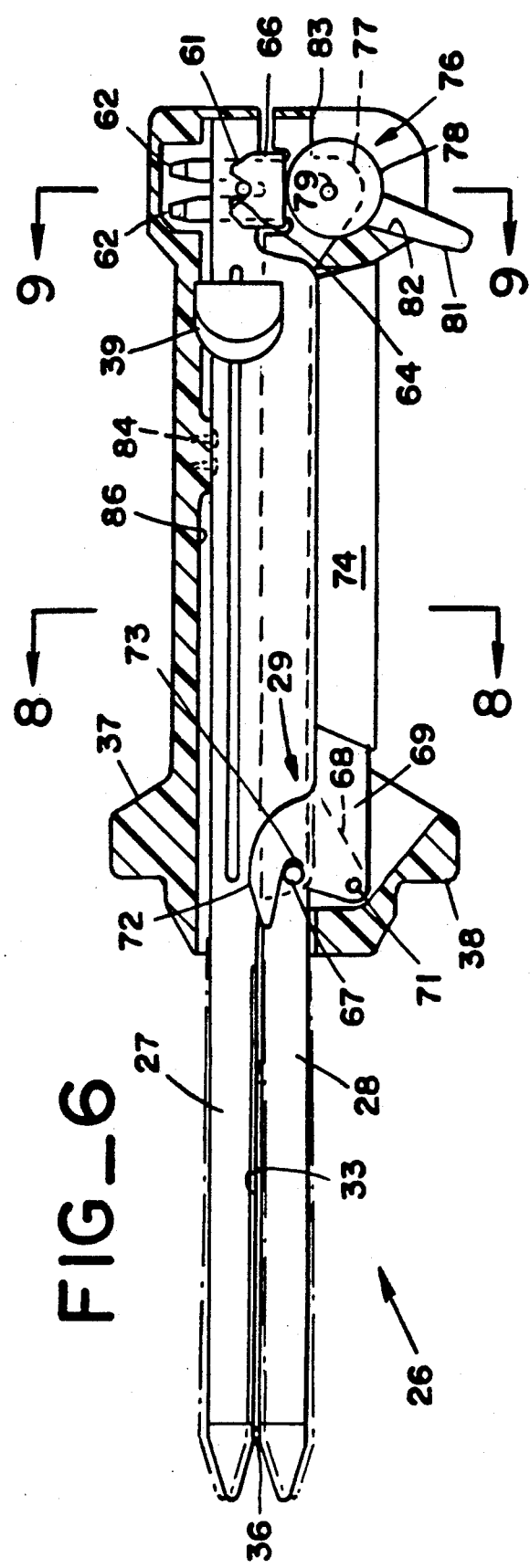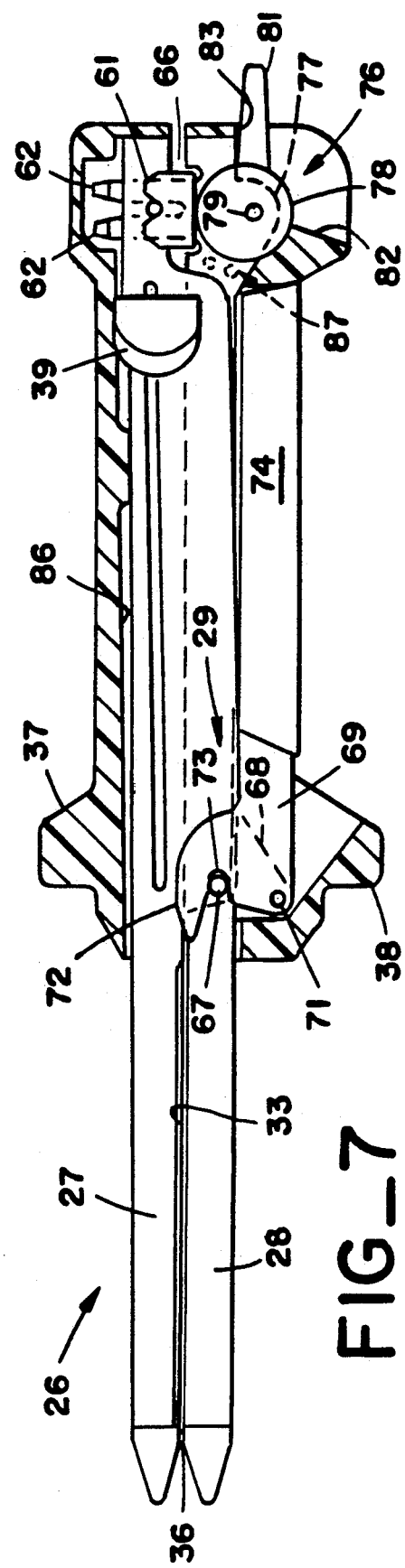

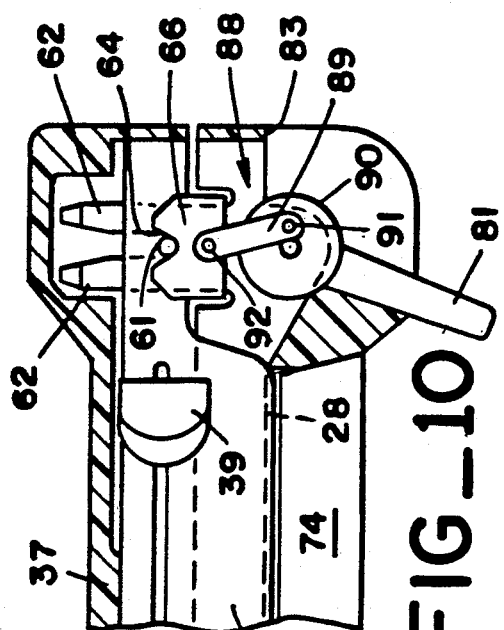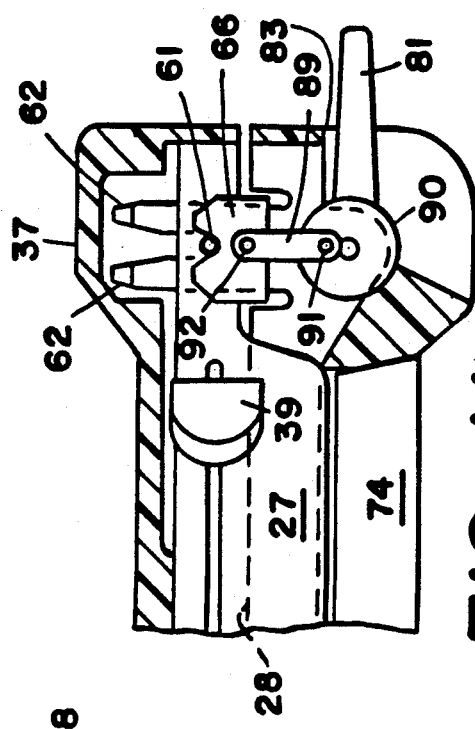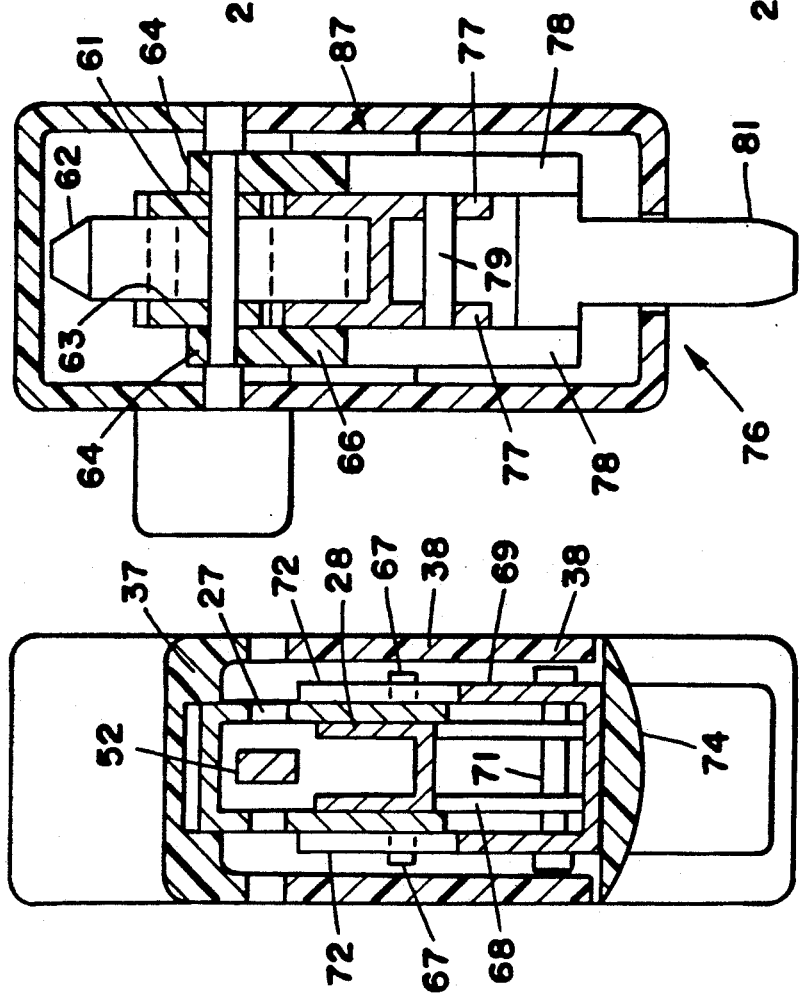

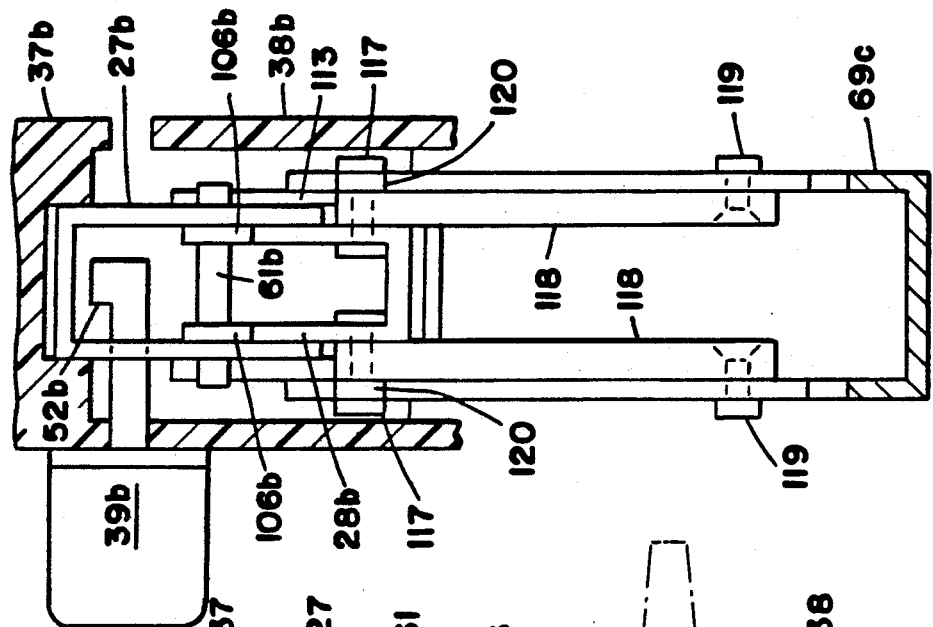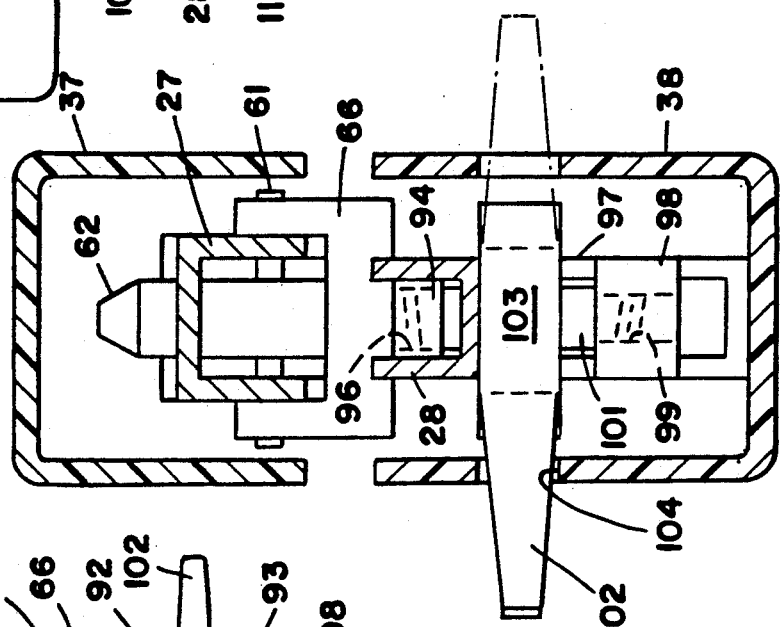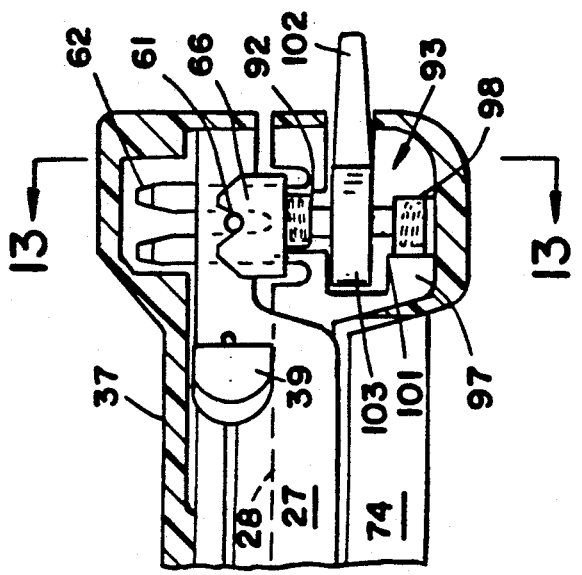

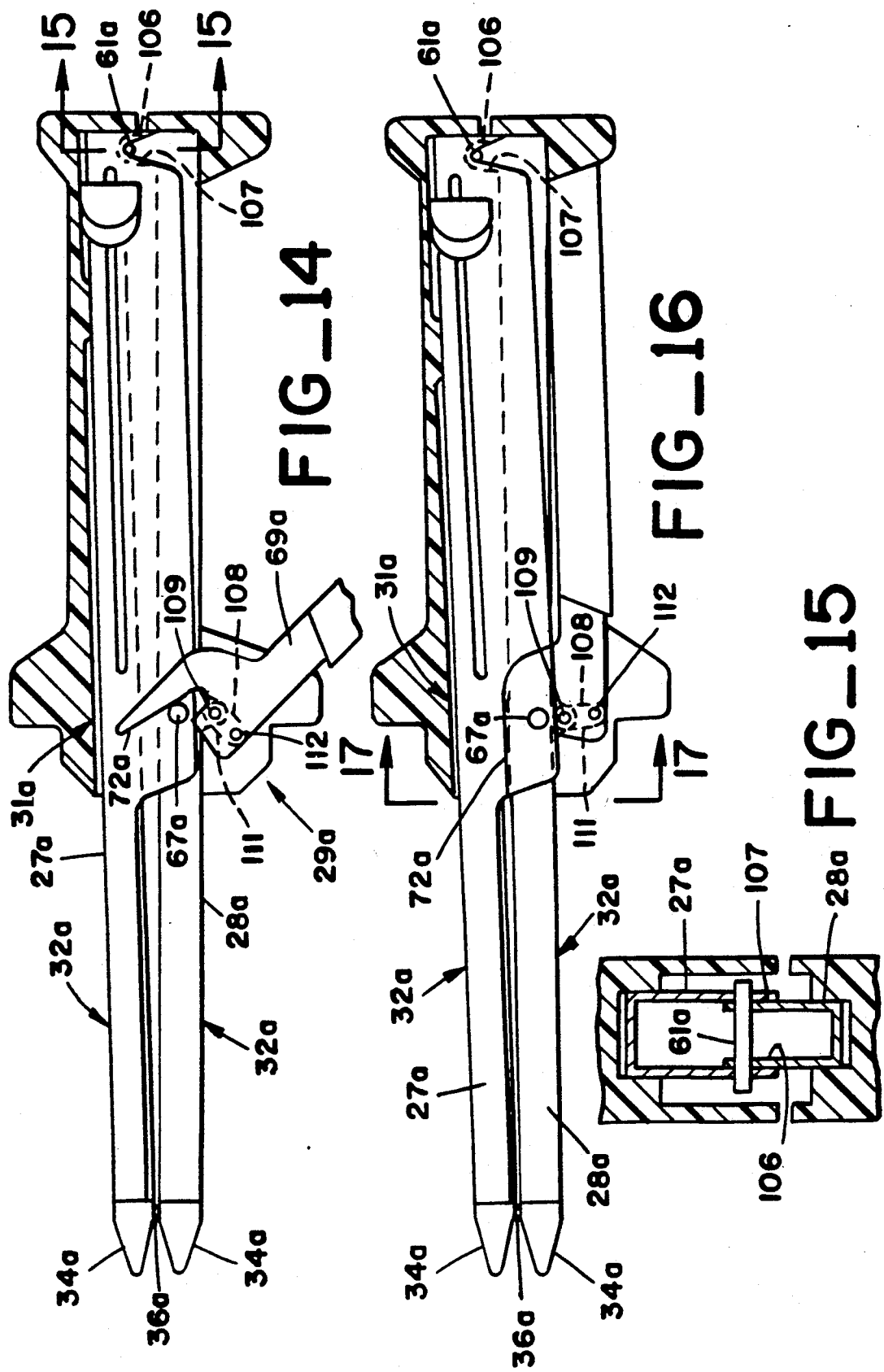

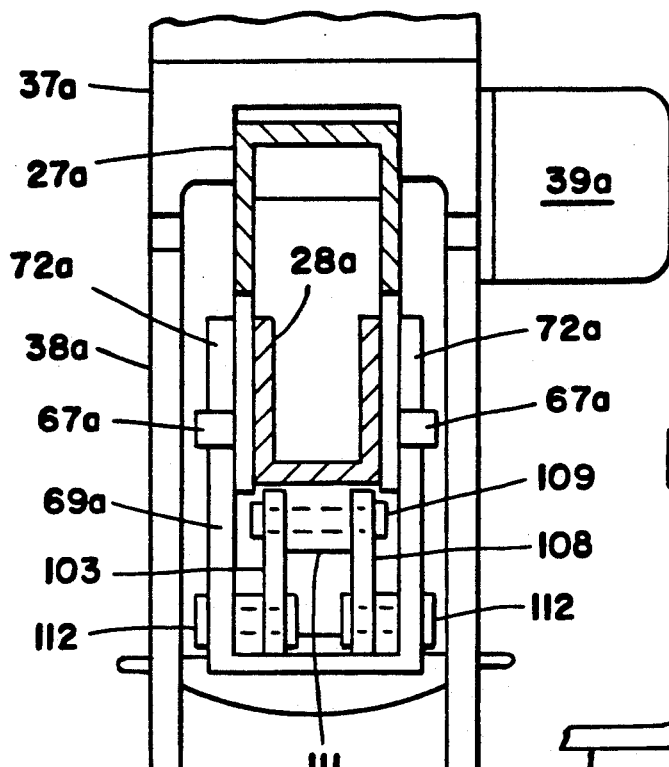
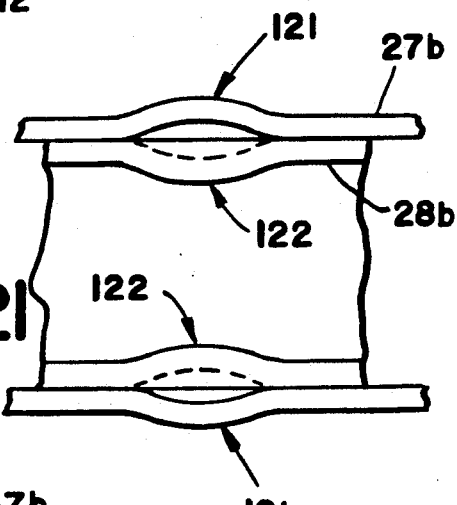
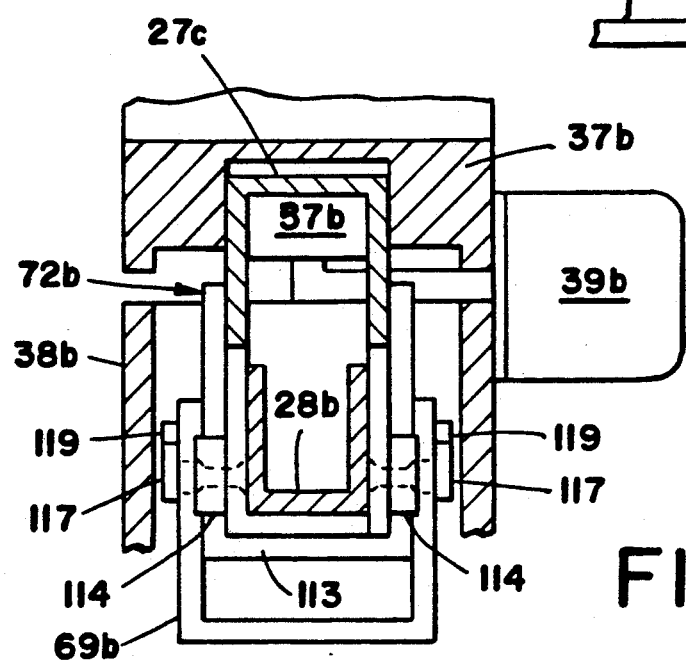

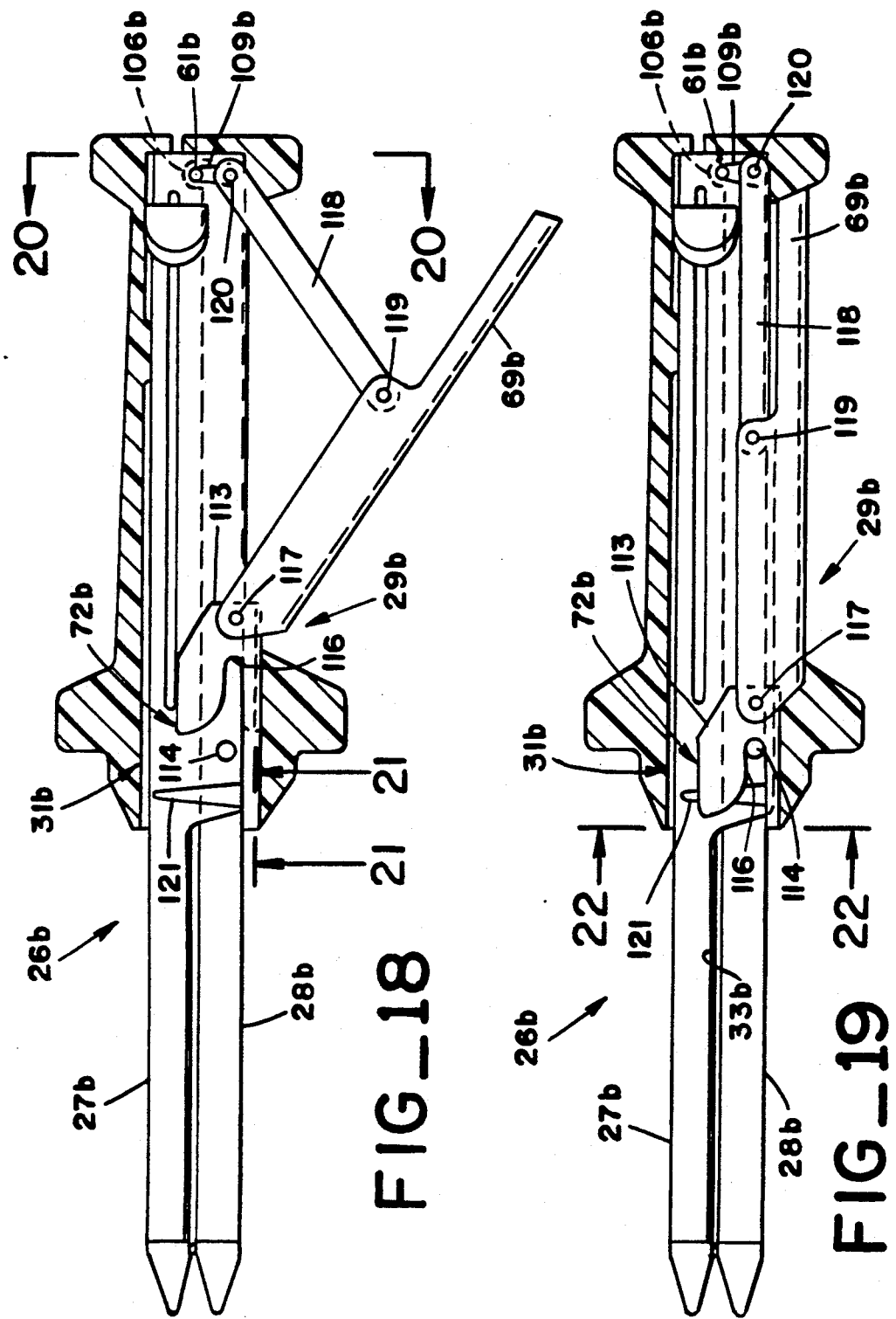

1

SURGICAL STAPLER

TECHNICAL FIELD

This invention relates to medical instruments and more particularly to staplers of the type used by surgeons for implanting rows of staples in living tissues during anastomotic procedures or the like.

BACKGROUND OF THE INVENTION

Various surgical procedures require suturing or joining of adjacent portions of a patient's tissues. In a gastrointestinal anastomosis, for example, two portions of tubular intestine are joined to form a single tubular body by disposing the two portions in parallel relationship, making a longitudinal cut through contacting walls of the two portions and suturing the edges of the two portions together along each side of the cut. Suturing of tissue along a linear zone is also performed on a number of other body organs in other surgical procedures.

Such medical procedures have been greatly facilitated by the use of stapling instruments to perform the suturing operation. Staplers of this kind have a pair of jaw or beam members with forward regions that define a thin gap in which the tissue is received and clamped. One of more rows of staples are contained within one of the beam members and an actuator is manually traveled along the instrument to sequentially force the staples out of the beam member and into the adjacent tissue. The other beam member has indentations shaped to bend and close the staples as they penetrate through the tissue. In some instruments of this type, parallel rows of staples are implanted simultaneously and the same movement of the actuator travels a knife edge along the tissue between the rows of staples to perform a tissue cutting operation concurrently with the implanting of staples.

The two beam members are usually separable to facilitate emplacement of the instrument. A lower beam member is placed under the tissue that is to be sutured and then the upper member is placed over the the tissue and coupled to the lower member by latching means located at an intermediate region along the the members. The latching means in conjunction with a small spacer projection located near the tip of one of the beam members spaces the forward portions of the beam members apart a small distance to establish a tissue receiving gap between the members.

The tissue receiving gap should be of a predetermined uniform size along the length of the gap during the stapling operation to assure that all staples are uniformly deformed into the optimum closed configuration. If the beam members in the region of the gap are not parallel at that time, compression of the successive staples is not uniform. Crunched staples and/or inadequately closed staples may be formed at different regions along the gap.

Maintaining a uniform tissue gap has been found to be difficult as there is a tendency for the tips of the beam members to be spread apart by forces which arise during the clamping of tissue and as a result of the forcing of staples through the tissue. The tissue thickness may vary from patient to patient and at different areas of a particular patients anatomy. The clamped tissue exerts a load force on the beam members that tends to deflect the members away from each other and this force becomes greater when the tissue is thicker than the instrument was designed for. Closing of the staples also tends to spread the beam members as significant force must be exerted in order to deform the staples into the closed configuration.

As the forward portions of the beam members are in an essentially cantilevered relationship, undesirable spreading of the tips becomes particularly pronounced if the length of the beam members and the tissue gap is increased as would be desirable for some surgical procedures.

Mechanisms have heretofore been devised for the purpose of assuring that the staples are uniformly formed into the optimum closed configuration along the length of the tissue receiving gap. Some prior surgical staplers with such mechanisms are effective for this purpose only if the clamped tissue has a thickness closely conforming to the thickness for which the instrument was designed. Other prior instruments of this type are more tolerant of variations of tissue thickness but have mechanism for resisting beam spreading that operates through the actuator which the surgeon travels along the instrument to sequentially implant the staples. This undesirably adds to the force which the surgeon must exert and may, under extreme loading conditions, create uncertain or misleading tactile feedback to the surgeon. Under those conditions, such mechanisms may create sudden and unanticipated increases in resistance to actuator travel. Among other effects, this can create the impression that stapling has been completed when that is not in fact the case.

The present invention is directed to overcoming one or more of the problems discussed above.

SUMMARY OF THE INVENTION

In one aspect of the present invention, a surgical stapler has first and second beam members with forward ends that are juxtaposed to jointly define a gap in which tissue may be received and clamped. The forward portion of the first beam member has means for receiving at least one row of staples and firing means for forcing the staples out of the receiving means and into the tissue. The forward portion of the second beam member has indentations shaped to close the staples as the staples are forced through the tissue. Tensioning means are provided for resisting spreading of the front ends of the beam members. The tensioning means flexes the beam members to create stress forces in the beam members that urge the front ends towards each other with sufficient force to prevent the spreading of the front ends. The stapler further includes means for selectively actuating the tensioning means independently of actuation of the firing means.

In another aspect of the invention, a surgical stapler for implanting one or more rows of staples in living tissue has first and second substantially linear beam members with front end regions spaced apart to form a tissue receiving gap. One of the beam members has mean for receiving at least one row of staples within the front end region of the beam member and firing means for sequentially forcing the staples out of the staple receiving means and into the tissue in response to translation of a first actuator element. The other of the beam members has staple tip receiving indentations shaped to close the staples as they penetrate through the tissue. A spacer projection extends from the front end region of one of the beam members towards the other beam member to establish a predetermined tissue gap width and a releasable latch couples the beam members together at an intermediate region along the beam members. A second actuator element on one of the beam members is movable from a first position to a second position independently of movement of the first actuator. The instrument further includes means for spreading the back end regions of the beam members apart in response to movement of the second actuator from the first position to the second position to create stress forces in the beam members that act to urge the front ends of the beam members towards each other.

In another aspect of the invention, a surgical stapler for implanting one or more rows of staples in living tissue has first and second substantially linear beam members with front end regions spaced apart to define a tissue receiving gap. One of the beam members has means for receiving at least one row of staples and firing means for sequentially forcing the staples into the tissue in response to translation of a first actuator element and the other beam member has indentations shaped to close the staples as they penetrate through the tissue. A spacer projection extends from the front end region of one of the beam members towards the other beam member to establish a predetermined tissue gap width. The beam members are convergent towards the front ends of the members when in an unstressed condition. A pair of latching pins extend outward from opposite sides of one of the beam members at an intermediate region along the member and a lever is pivoted to the other beam member, the lever being pivotable between a first position at which it is angled relative to the other beam member and a second position at which it extends along the back end region of the other beam member. The stapler further includes cam means for engaging the latching pins and drawing the intermediate regions of the beam members closer together as the lever is pivoted from the first position to the second position to bring the front regions of the members into a substantially parallel relationship and to create stress forces within the beam members that resist spreading of the front ends of the members.

In still another aspect, the invention provides a surgical stapler for implanting one or more rows of staples in living tissue which includes first and second juxtaposed beam members with front end regions spaced apart to form a tissue receiving gap, the beam members having a non-linear configuration which causes the front end regions of the members to be convergent and which also causes the back end regions of the members to be convergent when the members are in an unstressed condition. One beam member has means for receiving at least one row of staples and has firing means for sequentially forcing the staples into the tissue in response to translation of a first actuator element. The other beam member has staple tip receiving indentations which close the staples as they penetrate through the tissue. A spacer projection extends from the front end region of one of the beam members towards the other beam member to establish a predetermined tissue gap width. Latching pins extend outward from opposite sides of the intermediate region of one of the beam members and a lever is pivoted to the other beam member, the lever being pivotable between a first position at which it is angled relative to the other beam member and a second position at which it extends along the back end region of the other beam member. Further components include cam means for engaging the latching pins and drawing the intermediate regions of the beam members closer together as the lever is pivoted from the first position to the second position. This brings the front end regions of the beam members into a substantially parallel relationship and creates stress forces within the beam members which resist spreading of the front end regions of the members.

The invention provides a surgical stapler in which the beam members that define a tissue receiving gap are flexed to create internal stresses which strongly resist spreading of the beam tips. This assures that the gap will remain uniformly sized along its length when abnormally high load forces are present and thereby assures that each staple in a row of staples will be closed into the same optimum configuration. The beam tensioning means can be independently actuated prior to operation of the staple firing means. Thus the surgeon need not exert additional force during the staple firing operation for the purpose of resisting beam spreading. The tensioning means does not cause abrupt variations in the force needed to translate the staple firing actuator and thus does not produce potentially misleading tactile feedback to the surgeon during the staple firing operation.

The invention, together with further aspects and advantages thereof, may be further understood by reference to the following description of the preferred embodiments and by reference to the accompanying drawings.

BRIEF DESCRIPTION OF THE DRAWINGS

FIG. 1 is a side elevation view of a surgical stapler in accordance with a first embodiment of the invention.

FIG. 2 is a partially broken out top view of the surgical stapler of FIG. 1.

FIG. 3 is a cross section view of a portion of the surgical stapler of FIG. 1 taken along line 3—3 thereof.

FIG. 4 is a section view of the apparatus of FIG. 3 taken along line 4—4 thereof.

FIG. 5 is a diagramatic view depicting staple configurations which can be produced by a surgical stapler under varying conditions.

FIG. 6 is a side view of the surgical stapler of FIG. 1 shown with portions of the exterior housing thereof broken out in order to depict internal mechanism.

FIG. 7 is a view corresponding to FIG. 6 except that the internal mechanism is shown in a tensioned or stressed condition.

FIG. 8 is a cross section view of the surgical stapler of FIG. 6 taken along line 8—8 thereof.

FIG. 9 is a cross section view of the surgical stapler of FIG. 6 taken along line 9—9 thereof.

FIG. 10 is a broken out side view of the rear portion of a surgical stapler depicting a first modification of the apparatus of FIGS. 1 to 9.

FIG. 11 is a view corresponding to FIG. 10 except that the mechanism is shown in a tensioned or stressed condition.

FIG. 12 is a broken out side view of the rear portion of a surgical stapler depicting a second modification of the apparatus of FIGS. 1 to 9.

FIG. 13 is a Cross section view of the apparatus of FIG. 12 taken along line 13—13 thereof.

FIG. 14 is a side view of a surgical stapler in accordance with a second embodiment of the invention with the exterior housing of the apparatus broken out to expose interior mechanism.

FIG. 15 is a cross section view of a portion of the stapler of FIG. 14 taken along line 15—15 thereof.

FIG. 16 is a view corresponding to FIG. 14 except that the mechanism is shown in a tensioned or stressed condition.

FIG. 17 is a cross section view of the apparatus of FIG. 16 taken along line 17—17 thereof.

FIG. 18 is a side view of a surgical stapler in accordance with a third embodiment of the invention with the exterior housing of the apparatus broken out to expose interior mechanism.

FIG. 19 is a view corresponding to FIG. 18 except that the mechanism is shown in a tensioned or stressed condition.

FIG. 20 is a cross section view of the stapler of FIG. 18 taken along line 20—20 thereof.

FIG. 21 is a view of a portion of the underside of the stapler of FIG. 18 taken along line 21—21 thereof.

FIG. 22 is a cross section view of the stapler of FIG. 19 taken along line 22—22 thereof.

DETAILED DESCRIPTION OF THE PREFERRED EMBODIMENTS

Referring initially to FIGS. 1 and 2 of the drawings in conjunction, a surgical stapler 26 in accordance with a first embodiment of the invention has upper and lower beam members 27 and 28 respectively which are linear and parallel when in an unstressed condition. Latching means 29, to be hereinafter described in more detail, couples the beam members 27 and 28 together at an intermediate region 31 along the length of the members. The forward portions 32 of the beam members 27 and 28 that are in front of the intermediate region 31 are spaced apart a small distance to define a tissue receiving gap 33 between the members in which tissue may be clamped.

Bluntly pointed tips 34 extend forward from the front ends of beam members 27 and 28 to facilitate emplacement of the stapler 26 within a patient's body. A small spacer projection 36 extends from one of the tips 34 towards the other tip to establish a predetermined width for the gap 33, the term width being herein used to refer to the spacing of the beam members 27 and 28 in the region of gap 33. Latching means 29 establishes a similar beam member spacing at the back end of gap 33. The predetermined gap width may vary in different surgical staplers 26 that are designed for suturing different specific organs or tissues, 0.89 millimeters being a typical gap width in instruments designed for gastrointestinal anastomosis.

The portions of beam members 27 and 28 that are rearward from gap 33 are seated in housings 37 and 38 respectively that are shaped and proportioned to provide a comfortable grip for one of the surgeon's hands.

The upper beam member 27 including housing 37 is separable from the lower beam member 28 and housing 38 by disengagement of the latching means 29 as indicated by dashed lines in FIG. 1. This allows the separated lower beam member 28 to be positioned under the tissue which is to be sutured after which the upper beam member 27 may be placed over the lower beam member and tissue and the members may then be re-engaged by closing of the latching means 29. Cutting and and implanting of parallel rows of staples in the clamped tissue is then accomplished by manual translation of a firing means actuator element 39 forwardly along one side of the housings 37 and 38 which firing means will hereinafter be described in more detail. The upper and lower beam members 27 and 28 are then again disengaged from each other and removed from the patient's body.

Referring to FIG. 2 in particular, this embodiment of the stapler 26 is designed to implant four parallel rows 41 of staples 42 in the clamped tissue and to make a cut or incision through the tissue between the two innermost rows of staples following implanting of the staples. The pair of rows 41 of staples which are situated at each side of the cut are preferably offset longitudinally relative to each other to provide for a more complete suturing of the cut tissue. The invention is equally adaptable to staplers which implant other numbers of staples rows 41 and to staplers which do not make any cut or incision in conjunction with the implanting of staples.

Referring jointly to FIGS. 3 and 4, the upper beam member 27 has a channel shaped configuration and the rows 41 of staples 42 are initially contained within the forward portion of the member above tissue gap 33. Means 43 for receiving and storing the staples 42 within upper beam member 27 and the firing means 44 for sequentially forcing the staples into tissue 46 that is clamped between beam members 27 and 28 may be of any the forms known to the art, examples of which are described in U.S. Pat. Nos. 4,633,874 and 3,490,675. The staple receiving means 43 may, for example, include a replacable cartridge 47 shaped to fit within the forward portion 32 of upper beam member 27. The beam member 27 is formed of steel o similar resilient material and cartridge 47 is proportioned to expand the beam member very slightly as it is seated causing the resiliency of the beam member to hold the cartridge in place.

The staples 42 are arranged in the desired rows 41 within cartridge 47 and each staple is situated within a separate passage 48 which extends to the undersurface of the cartridge. A staple driver 49 extends upward from the staple 42 in each such passage 48. Firing means 44 may include a wedge like element 51 within upper beam member 27 that is coupled to the translatable firing means actuator 39 by a drive rod 52 and which is traveled into the cartridge 47 and along the rows of staple drivers 49 by forward movement of the actuator 39. The wedge like element 51 has a slanting undersurface 53 which forces each staple driver 49 and thus the underlying staple 42 downward into the tissue 46 that is clamped within gap 33 as the element 51 is traveled to the front end of beam member 27.

The lower beam member 28 also has a channel shaped configuration except at the forward region 32 which is below tissue gap 33 where the member 28 is formed to have an anvil surface 54 that faces the underside of staple cartridge 47. Arcuate indentations 56 in the anvil surface 54 are shaped and located to receive the tips of staples 42 as they penetrate through tissue 46 and to deform the staples into the closed configuration which is essentially a B-shaped configuration in this example.

If the surgical stapler is designed to make an incision along tissue 46 following the implanting of staples 42, a slot 57 extends along the center of cartridge 47 below the path of travel of the previously described wedge element 51 of the firing means and another slot 58 extends along the center of anvil surface 54. A thin knife blade 59 is carried by the element 51 and extends down through the slots 57 and 58.

The beam members 27 and 28 must be precisely registered with each other to assure that the tips of staples 42 enter the anvil surface indentations 56. Referring jointly to FIGS. 6 and 8, the portion of the upper beam member 27 that is rearward from tissue gap 33 has a height slightly greater than twice the height of the lower beam member 28 and is sufficiently broad to extend downward along opposite sides of the lower beam member 28 thereby assuring a precise lateral registration of the two members.

Referring to FIGS. 6 and 9, longitudinal registration of the beam members 27 and 28 is provided for by a registration pin 61 which extends transversely across the back end region of upper beam member 27 and which extends a small distance outward from each side of member 27. The central portion of the transverse register pin 61 is received between two projections 62 that extend upward from the lower beam member 28 and through an opening 63 in the top of the upper beam member 27, the projections 62 being spaced apart along the lower beam member a distance corresponding to the diameter of pin 61. The outwardly projecting ends of pin 61 also seat in slots 64 at each side of a sleeve 66 that is vertically slidable along projections 62 for purposes to be hereinafter described.

Referring jointly to FIGS. 6 and 8, latching means 29 includes a pair of latching pins 67 each of which extends a short distance outward from an opposite side of upper beam member 27 at a location which is a short distance behind and below the tissue gap 33. A pair of tangs 68 extend downward from lower beam member 28 beneath pins 67 and the front end of a latching lever 69 is coupled to the tangs by a pivot pin 71. The front end of lever 69 is formed with a pair of curved cam fingers 72 each of which extends up along an opposite side of lower beam member 28 and each of which has a notch 73 for receiving one of the latching pins 67. Lever 69, which may have a rounded handle member 74 extending along its underside, may be pivoted from an unlatched position depicted by dashed lines in FIG. 1 to a latched position, shown in FIGS. 6 and 8, at which it extends along the rear portion of the lower beam member 28. Cam fingers 72 are shaped to engage the latching pins 67 as the lever 69 is pivoted towards the Closed position and to seat the pins in notches 73 thereby locking the upper and lower beam members 27 and 28 together.

The rear register pin 61 and latching pins 67 are located to cause the back end of tissue gap 33 to have the same width that is established at the front end of the gap by spacer projection 36 so that the gap has a uniform size throughout its length. Pivot pin 71 is located slightly forward from latching pins 67 so that any force that tends to pull the beam members 27 and 28 apart also acts to hold the lever 69 in the closed position thereby preventing separation of the members.

The surgical stapler 26 is operable when in the condition depicted in FIG. 6 but, in common with earlier forms of stapler, would be susceptible to deflection or spreading of the front portions 32 of the beam members 27 and 28 as depicted by dashed lines in the figure if very strong load forces are experienced as a result of clamping unusually thick layers of tissue or for other reasons. Such spreading causes a non-uniform closure of the staples along a row as depicted in FIG. 5. Staples 42-1 at the rear of the tissue gap may be closed in the desired manner but as illustrated by staples 42-2 and 42-3, the staple closures become progressively less complete towards the front of the tissue gap. Staple 42-4 illustrates an over closure or crunched condition that can occur at the forward end of the tissue gap when light tissue loads are present if the gap is shaped to taper towards the front in an effort to compensate for deflections that may occur under heavy loading.

Referring again to FIG. 6, the stapler 26 of the present invention includes tensioning means 76 for flexing the beam members 27 and 28 to create internal stress forces within the members that act to urge the tips 34 of the members towards each other with sufficient force to prevent spreading of the tips under high loading conditions. In the present embodiment, the tensioning means 76 creates such stress forces by spreading the back ends of beam members 27 and 28 apart as depicted in FIG. 7. The latching means 29 prevent spreading of the intermediate regions 31 of the beam members 27, 28 and thus energy is stored in the resilient material of beam members 27 and 28 that acts to resist spreading of the front portions of the members.

Referring again to FIGS. 6 and 9, an additional pair of tangs 77 extend downward from opposite sides of lower beam member 28 at the back end of the member. The tensioning means 76 of this embodiment includes a pair of circular cams 78 disposed at opposite sides of the lower beam member 28 and which are journalled to tangs 77 by a transverse axle 79. A tensioning means actuator lever 81 is secured to both cams 78 and extends out of housing 38 to enable manual turning of the cams.

Axle 79 is offset from the centers of cams 28 and the peripheries of the cams ride against the underside of the previously described sleeve 66 on which register pin 61 is seated and which functions as a cam follower. Thus turning of the actuator lever 81 from the position shown in FIG. 6 to the position shown in FIG. 7 forces sleeve 66 and register pin 61 upward along projections 62. As the register pin 61 is attached to upper beam member 27, this forces the back ends of the two beam members apart to create the above discussed stress forces within the members.

Downward pivoting of lever 81 is limited by a first surface 82 within housing 38 that is contacted by the lever when sleeve 66 is at its lowest position and the tensioning means is unactuated. Another housing surface 83 is located to limit upward pivoting of the lever 81 when the members 27 and 28 are fully tensioned. Upper housing 37 is fastened to upper beam member 27, by screws 84 or the like, at only one small area along the length of the member 27. A small vertical clearance 86 is provided between other areas of the top surface of beam member 27 and the housing 37. Similarly, the lower housing 38 is fastened to lower beam member 28 at only one location 87 along the length of the member. Consequently, the relatively rigid housings 37 and 38 do not interfere with the slight flexing of the beam members that creates the above described stress forces.

The construction of beam tensioning means 76 may be varied in a number of ways. The cams 78 may, for example, be replaced with a toggle linkage 88 as shown in FIG. 10. The eccentric cams are replaced with circular discs 90 which are concentric with the axis of axle 79. A pair of toggle links 89, of which only one appears in FIG. 10, have lower ends coupled to the discs 90 by pivot couplings 91 and upper ends connected to sleeve 66 by additional pivot couplings 92. Pivot couplings 91 are offset from axle 79. Thus turning of actuator lever 81 from the position shown in FIG. 10 to the position shown in FIG. 11 raises sleeve 66 and tensions the beam members 27 and 28 as previously described.

Referring to FIGS. 12 and 13 in conjunction, a screw threaded actuator 93 may also be used to spread the back ends of beam members 27 and 28 to tension the members. In this example, sleeve 66 has a downwardly directed extension 94 with an internally threaded passage 96. A downward extension 97 at the rear region of lower beam member 28 supports another element 98 having another vertically directed internally threaded passage 99. The threads within passages 96 and 99 have opposite pitches, passage 96 having right hand threads in this example while passage 99 contains left hand threads. A turnable shaft 101 has upper and lower ends which extend into passages 96 and 99 respectively and which are threaded to engage with the threads in the passages. A tensioner actuator lever 102 is secured to a disc like enlargement 103 on shaft 101 and extends out of housing 38 through a transverse slot 104 at the back of housing 38. Thus the back ends of beam members 27 and 28 may be forced apart to tension the members by pivoting lever 102 in one direction and the tension may be released by pivoting the lever in the opposite direction.

In the above described embodiment stressing or tensioning of members 27 and 28 is effected by forcing the back ends of the members apart. Tensioning can also be brought about in other ways. Referring jointly to FIGS. 14 and 15, for example, the upper and lower beam members 27a and 28a respectively can be inclined relative to each other to cause the forward portions 32a of the members to be slightly convergent towards the front ends of the members when the members are in the untensioned condition. This orientation may be realized by locating the transverse rear register pin 61a to extend between a pair of tangs 106 which extend upward from the back end of lower beam member 28a. The pin 61a seats in notches 107 in the side walls of the channel shaped upper beam member 27a. Tangs 106 are in effect rear spacer projections of sufficient height to establish the above described convergency of beam members 27a and 28a when the front spacer projection 36a on one beam member tip 34a is in contact with the other tip 34a and the beam members are in an unstressed condition.

The latching means 29a in this embodiment also functions as the tensioning means. The cam fingers 72a of the latching lever 69a engage the latching pins 67a of upper beam member 27a essentially as previously described but in this case are shaped to draw the intermediate regions 31a of the beam members closer together as the latching lever is pivoted backward towards the latched position of the lever. This flexes the beam members 27a and 28a to bring the forward portions of the members into a parallel relationship and thereby establishes a tissue gap 33 that is of uniform size throughout its length as depicted in FIG. 16. Such flexing of the beam members 27a and 28a also creates the stress forces within the members that strongly resist spreading of tips 34a by load forces.

Operation of the latching lever 69a requires somewhat more force than in the case of the previously described embodiment as the lever movement must flex the beam members 27a and 27b in addition to simply latching the members together. Referring to FIGS. 16 and 17, the effort required for lever operation can be reduced by modifying the previously described direct pivoting of the lever to lower beam member 28a. In particular, a pair of short, spaced apart links 108 have upper ends pivoted by an axle 109 to opposite sides of a tang 111 that extends down from lower beam member 28a. The lower ends of links 108 are pivoted to opposite sides of latching lever 69a by additional pivot couplings 112. Pivot axle 109 is directly below latching pins 67a while pivot couplings 112 are located slightly closer the back end of the stapler 26a so that the stress forces in beam members 27a and 28a resist movement of the lever out of the latched position. Coupling of lever 69a to lower beam member 28a through the links 108 results in an increasing mechanical advantage, and therefore less effort on the part of the operator, as the lever approaches the latched position. If the lever is directly pivoted to lower beam member 28a an increasing force must be applied as the lever approaches that position because of the build-up of stress within the beam members 27a and 28a.

Except as herein described, components of the stapler 26a may be similar to those of the previously described embodiment.

FIGS. 18 and 19 depict another embodiment of the surgical stapler 26b in which tensioning of the beam members 27a and 27b is accomplished in still another way. The upper and lower beam members 27b and 28b in this embodiment are formed to be non-linear when in the unstressed condition and have a slight curvature or bend which causes the beam members to be convergent towards both the front ends and the back ends of the members under that condition. Actuation of a modified latching and tensioning means 29b flexes the beam members 27b and 28b into a linear configuration and parallel relationship as depicted in FIG. 19 thereby causing the tissue gap 33b to be of uniform size along its length.

Referring jointly to FIGS. 18 and 20, the transverse rear register pin 61b may again be supported by a pair of tangs 106b that extend upward from the back end of lower beam member 28b and which extend slightly outward at each side of the member. The ends of the register pin again seat in vertically directed notches 109b in the sides of the upper beam member 27b. The tangs 106b need not be of the same height as in the previously described embodiment since the beam members 27b and 28b are convergent towards their back ends in this embodiment.

The latching means 29b of this embodiment, which also functions as the tensioning means, includes a slidable channel shaped shoe 113 which bridges the underside of beam members 27b and 28b and which has a pair of cam fingers 72b that extend upward and forwardly at opposite sides of the upper beam member 27b. Shoe 113 is slidable in a forward and backward direction and, when traveled in the forward direction, cam finger 72b engage a pair of latching rollers 114 which are journalled to the upper beam member 27b at opposite sides of the member. Cam fingers 72b are shaped to draw the rollers 114 downward as the shoe 113 is slid forward and have notches 116 in which the rollers seat when the beam members 27b, 28b have been flexed into a linear configuration and parallel relationship as shown in FIG. 19.

Shoe 113 is travelled, to latch and tension the beam members 27b and 28b and to disengage the members, by pivoting of a latching lever 69b which has a forward end pivoted to the shoe 113 by pivot couplings 117. Referring jointly to FIGS. 18 and 20, a pair of toggle links 118 each have forward ends pivoted to opposite sides of latching lever 69b at an intermediate location along the length of the lever by pivot couplings 119. The back ends of links 118 are pivoted to the back end of lower beam member 28b by additional pivot couplings 119.

Thus when latching lever 69b is pivoted away from the back end of lower beam member 28b as shown in FIG. 18, shoe 113 is drawn rearwardly and fingers 72b release rollers 114. This disconnects the beam members 27b and 28b and also allows the beam members to spring back to their non-linear unstressed configuration. Reverse pivoting of the latching lever 69b into a substantially parallel relationship with beam members 27b, 28b as shown in FIG. 19 drives the shoe 113 forward to latch the beam members 27b and 28b together and to flex the members into a linear parallel relationship as described above.

Pivot couplings 119 are preferably located to be slightly above the level of pivot couplings 117 and 120 when the apparatus is in the latched and tensioned condition shown in FIG. 19 and the links 118 are proportioned to cause shoe 113 to exert pressure against rollers 114 as the latching movement of lever 69b is completed. The resulting longitudinal compression of the lever 69b and links 118 assembly creates a stress force in such elements that acts to resist unlatching of the mechanism and holds the lever in the latched position until such time as it is forcibly pivoted away from the beam members 27b and 28b.

Referring to FIGS. 18 and 21, the degree of manual effort that is needed to tension beam members 27b and 28b and latch the stapler 26b by pivoting of lever 72b can be reduced by providing a slight outward bulge 121 in each sidewall of upper beam member 27b at an intermediate location therealong. Bulges 121 extend upward from the base of beam member 27b and are tapered to become progressively smaller towards the top of the member. Inwardly directed bulges 122 may also be provided at a corresponding location along the sidewalls of the lower beam member 28b which bulges are broadest at the top of the lower beam member and become progressively smaller towards the base of that member. The bulges 121 and 122, which flatten out as the beam members 27b and 28b are tensioned, establish a predetermined localized zone at which the flexing of the beam members occurs.

Lengthening the tissue gap of a conventional surgical stapler increases the susceptibility of the instrument to tip spreading by load forces. The strong resistance to spreading of the beam member tips that is realized with the present invention is advantageous in staplers of any size but also enables use of instruments having very long tissue gaps as would be desirable for a number of medical purposes. An example of the present invention having a 100 millimeter tissue gap has been found to be free of significant tip spreading when subjected to strong load forces.

While the invention has been described with respect to certain specific embodiments for purposes of example, many modifications and variation of the construction are possible and it is not intended to limit the invention except as defined in the following claims.

I claim:

1. A surgical stapler for implanting one or more rows of staples in living tissue, said stapler having first and second beam members each having a front end and a back end and an intermediate region situated therebetween, said beam members further having forward portions situated between said front ends and said intermediate regions which are juxtaposed to jointly define a gap in which said tissue may be received and clamped, said forward portion of said first beam member having means for receiving at least one row of staples and firing means for forcing said staples out of said receiving means and into said tissue in response to movement of a firing means actuator, said forward portion of said second beam member having indentation shaped to close said staples as said staples are forced through said tissue, wherein the improvement comprises:

tensioning means for flexing and prestressing said beam members prior to operation of said firing means to create stress forces therein that urge said front ends of said beam members towards each other with sufficient force to prevent spreading of said front ends thereof by the load forces exerted on said beam members, and means for selectively actuating said tensioning means prior to and independently of movement of said firing means actuator.

2. The surgical stapler of claim 1 wherein said firing means actuator is disposed on one of said beam members and is manually translated therealong to force said staples into said tissue and wherein said means for selectively actuating said tensioning means includes a separate actuator on one of said beam members which may be manually moved from a first position to a second position and wherein said tensioning means applies bending forces to said beam members in response to movement of said separate actuator from said first position thereof to said second position thereof.

3. The surgical stapler of claim 1 further including means for holding said first and second beam members together at said intermediate regions thereof and wherein said tensioning means urges said back ends of the beam members away from each other prior to movement of said firing means actuator.

4. The surgical stapler of claim 3 wherein said tensioning means includes a cam journalled to one of said members and being turnable about an axis which is offset from the center of the said cam, a cam follower in contact with aid cam and which is translated by said turning thereof, and an element on the other of said members which seats on said cam follower whereby said turning of said cam urges said back end of said other member away from said back end of said one member.

5. The surgical staples of claim 1 further including a front spacer projection extending from one of said beam members towards the other thereof in the vicinity of said front ends of said beam members to establish a predetermined width for said gap and wherein said tensioning means includes a rear spacer projection extending from one of said beam members toward the other thereof in the vicinity of said back ends of said beam members, said rear spacer projection being proportioned to hold said back ends of said beam members apart a distance that is sufficient to cause said beam members to be convergent towards said front ends thereof when said beam members are in an unstressed condition and wherein actuation of said tensioning means draws said intermediate regions of said beam members towards each other to cause said gap to have a substantially uniform width along the length thereof.

6. The surgical stapler of claim 1 wherein one of said beam members has a pair of pins which extend outward therefrom at opposite sides of said intermediate region thereof and wherein said tensioning means includes a lever pivoted to the other of said beam members at said intermediate region thereof and which is pivotable between first and second positions, said lever having cam fingers at each side of said beam members which are shaped to engage said pins and latch said intermediate regions of said beam members together as said lever is pivoted from said first position thereof to said second position thereof and to flex said beam members and create stress therein which resists spreading of said front ends thereof.

7. The surgical stapler of claim 6 wherein said intermediate regions of said beam members are spaced further apart than said front ends of said beam members when said beam members are in an unstressed condition and wherein said cam fingers are shaped to draw said intermediate regions of said beam members closer together as said lever is pivoted from said first position thereof to said second position thereof.

8. The surgical stapler of claim 6 wherein said lever is angled relative to said beam members when at said first position and is substantially parallel to said beam members and extends along the back end regions thereof when at said second position and wherein said lever is pivoted to said one beam member at a location which is further from said back ends of said beam members than said pins when said lever is at said second position whereby said tensioning of said beam members acts to resist movement of said lever away from said second position thereof.

9. The surgical stapler of claim 1 wherein one of said beam members has a pair of latching elements which extend outward therefrom at opposite sides of said intermediate region thereof and wherein said tensioning means includes a shoe slidable along the other of said beam members between said intermediate region and said back end thereof, said shoe having a pair of cam fingers situated at opposite sides of said beam members shaped to engage said latching elements and to draw said intermediate regions of said beam members together as said shoe is slid forward to said intermediate region.

10. A surgical stapler for implanting one or more rows of staples in living tissue, said stapler having first and second beam members each having a front end and a back end and an intermediate region situated therebetween, said beam members further having forward portions situated between said front ends and said intermediate regions which are juxtaposed to jointly define a gap in which said tissue may be received and clamped, said foward portion of said first beam member having means for receiving at least one row of staples and firing means for forcing said staples out of said receiving means and into said tissue, said forward portion of said second beam member having indentations shaped to close said staples as said staples are forced through said tissue, wherein the improvement comprises:

tensioning means for resisting spreading of said front ends of said beam members by load forces exerted thereon which tensioning means flexes said beam members to create stress forces therein that urge said front ends of said beam members towards each other with sufficient force to prevent said spreading of said front ends thereof, means for selectively actuating said tensioning means independently of actuation of said firing means, further including means for holding said first and second beam members together at said intermediate regions thereof and wherein said tensioning means urges said back ends of said beam members away from each other, further including a register pin secured to one of said beam members at a location behind said intermediate region thereof and wherein said tensioning means includes a projection extending toward said register pin from the other of said beam members at a location behind said intermediate region thereof, a sleeve slidable along said projection and having a slot in which said register pin seats, a first toggle member mounted on said other beam member and being turnable about an axis of rotation that is orthogonal to said projection and a toggle link having one end pivotably coupled to said sleeve and an opposite end which is pivotably coupled to said first toggle member at a location offset from said axis of rotation thereof.

11. A surgical stapler for implanting one or more rows of staples in living tissue, said stapler having first and second beam members each having a front end and a back end and an intermediate region situated therebetween, said beam members further having forward portions situated between said front ends and said intermediate regions which are juxtaposed to jointly define a gap in which said tissue may be received and clamped, said forward portion of said first beam member having means for receiving at least one row of staples and firing means for forcing said staples out of said receiving means and into said tissue, said forward portion of said second beam member having indentations shaped to close said staples as said staples are forced through said tissue, wherein the improvement comprises:

tensioning means for resisting spreading of said front ends of said beam members by load forces exerted thereon which tensioning means flexes said beam members to create stress forces therein that urge said front ends of said beam members towards each other with sufficient force to prevent said spreading of said front ends thereof, means for selectively actuating said tensioning means independently of actuation of said firing means, further including means for holding said first and second beam members together at said intermediate regions thereof and wherein said tensioning means urges said back ends of said beam members away from each other, further including a register pin secured to one of said beam members at a location behind said intermediate region thereof and wherein said tensioning means includes a projection extending towards said register pin from the other of said beam members at a location behind said intermediate region thereof, a sleeve slidable along said projection and having a slot in which said register pin seats and having a first threaded passage, said other beam member having a second threaded passage aligned with said first threaded passage, one of said threaded passages having right hand threads and the other of said passages having left hand threads, further including a screw having opposite ends extending into each of said passages and having right hand threads at one end that engage with said threads of said one passage and left hand threads at the other end that engage with said threads of said other passage whereby turning of said screw in a predetermined direction forces said back ends of said beam members apart.

12. A surgical stapler for implanting one or more rows of staples in living tissue, said stapler having first and second beam members each having a front end and a back end and an intermediate region situated therebetween, said beam members further having forward portions situated between said front ends and said intermediate regions which are juxtaposed to jointly define a gap in which said tissue may be received and clamped, said foward portion of said first beam member having means for receiving at least one row of staples and firing means for forcing said staples out of said receiving means and into said tissue, said forward portion of said second beam member having indentations shaped to close said staples as said staples are forced through said tissue, wherein the improvement comprises:

tensioning means for resisting spreading of said front ends of said beam members by load forces exerted thereon which tensioning means flexes said beam members to create stress forces therein that urge said front ends of said beam members towards each other with sufficient force to prevent said spreading of said front ends thereof, means for selectively actuating said tensioning means independently of actuation of said firing means, wherein said first and second beam members have a non-linear configuration which causes said beam members to be convergent towards said front ends thereof and to also be convergent towards said back ends thereof when said beam members are in an unstressed condition, and wherein actuation of said tensioning means draws said intermediate regions of said beam members closer together to flex said beam members into a substantially linear configuration and a substantially parallel relationship.

13. The surgical stapler of claim 12 wherein said beam members have elements in the vicinity of said back ends thereof which mate with each other to establish an abutment of said beam members in the region of said back ends thereof, further including a front spacer projection extending from one of said beam members to the other thereof in the vicinity of said front ends thereof to establish a predetermined width for said gap and wherein actuation of said tensioning means causes the spacing of said intermediate regions of said beam members to correspond to the spacing of said front ends of said beam members that is established by said front spacer projection whereby said tissue receiving gap becomes of substantially uniform width along the length of said gap.

14. A surgical stapler for implanting one or more rows of staples in living tissue, said stapler having first and second beam members each having a front end and a back end and an intermediate region situated therebetween, said beam members further having forward portions situated between said front ends and said intermediate regions which are juxtaposed to jointly define a gap in which said tissue may be received and clamped, said foward portion of said first beam member having means for receiving at least one row of staples and firing means for forcing said staples out of said receiving means and into said tissue, said forward portion of said second beam member having indentations shaped to close said staples as said staples are forced through said tissue, wherein the improvement comprises:

tensioning means for resisting spreading of said front ends of said beam members by load forces exerted thereon which tensioning means flexes said beam members to create stress forces therein that urge said front ends of said beam members towards each other with sufficient force to prevent said spreading of said front ends thereof, means for selectively actuating said tensioning means independently of actuation of said firing means, and wherein one of said beam members has a pair of pins which extend outward therefrom at opposite sides of said intermediate region thereof and wherein said tensioning means includes a lever pivoted to the other of said beam members at said intermediate region thereof and which is pivotable between first and second positions, said lever having cam fingers at each side of said beam members which are shaped to engage said pins and latch said intermediate regions of said beam members together as said lever is pivoted from said first positions thereof to said second position thereof, and wherein said lever is angled relative to said beam members when at said first position and is substantially parallel to said beam members and extends along the back end regions thereof when at said second position, further including a pair of toggle links situated at opposite sides of said beam members, each of said links having a first end pivoted to said one beam member at a first location therealong and an opposite end pivoted to said lever at a second location which is further away from said beam members and situated more rearwardly therealong than said first location when said lever is at said second position whereby said tensioning of said beam members acts to resist movement of said lever away from said second position thereof.

15. A surgical stapler for implanting one or more rows of staples in living tissue, said stapler having first and second beam members each having a front end and a back end and an intermediate region situated therebetween, said beam members further having forward portions situated between said front ends and said intermediate regions which are juxtaposed to jointly define a gap in which said tissue may be received and clamped, said foward portion of said first beam member having means for receiving at least one row of staples and firing means for forcing said staples out of said receiving means and into said tissue, said forward portion of said second beam member having indentations shaped to close said staples as said staples are forced through said tissue, wherein the improvement comprises:

tensioning means for resisting spreading of said front ends of said beam members by load forces exerted thereon which tensioning means flexes said beam members to create stress forces therein that urge said front ends of said beam members towards each other with sufficient force to prevent said spreading of said front ends thereof, means for selectively actuating said tensioning means independently of actuation of said firing means, and wherein one of said beam members has a pair of latching elements which extend outward therefrom at opposite sides of said intermediate region thereof and wherein said tensioning means includes a show slidable along the other of said beam members between said intermediate region and said back end thereof, said shoe having a pair of cam fingers situated at opposite sides of said beam members shaped to engage said latching elements and to draw said intermediate regions of said beam members together as said shoe is slid forward to said intermediate region, further including a latching lever having an end pivoted to said shoe by a first pivot coupling and a toggle link having a front end pivoted to said lever by a second pivot coupling and an opposite end pivoted to said other beam member by a third pivot coupling situated reawardly from said intermediate region of said other beam member, said lever and link being pivotable into alignment with each other as said shoe is engaged with said latching elements, said second pivot coupling being located above the level of said first and third pivot couplings when said lever and link are in alignment.

16. A surgical stapler for implanting one or more rows of staples in living tissue comprising:
first and second substantially linear beam members each having a front end region, an intermediate region and a back end region, said front end regions being spaced apart to form a tissue receiving gap therebetween, one of said beam members having means for receiving at least one row of staples within said front end region thereof and firing means for sequentially forcing said staples out of said staple receiving means and into said tissue in response to translation of a first actuator element, the other of said beam member having staple tip receiving indentations shaped to close said staples as said staples penetrate through said tissue, one of said beam members having a spacer projection extending towards the other of said beam members at said front end region thereof to establish a predetermined width of said gap
a releasable latch adapted to couple said beam members together at said intermediate regions thereof,
a second actuator element on one said beam members, said second actuator element being movable from a first position to a second position prior to and independently of movement of said first actuator element, and means for spreading said back end regions of said beam members apart in response to movement of said second actuator element from said first position thereof to said second position thereof to create stress forces in said beam members that act to urge said front end regions towards each other.

17. A surgical stapler for implanting one or more rows of staples in living tissue comprising:
first and second substantially linear beam members each having a front end region, an intermediate region and a back end region, said front end regions being spaced apart to form a tissue receiving gap therebetween, one of said beam members having means for receiving at least one row of staples within said front end region thereof and firing means for sequentially forcing said staples out of said staple receiving means and into said tissue in response to translation of a first actuator element, the other of said beam members having staple tip receiving indentations shaped to close said staples as said staples penetrate through said tissue, one of said beam members having a spacer projection extending towards the other of said beam members at said front end region thereof to establish a predetermined width of said gap, said beam members being convergent towards said front end regions thereof when in an unstressed condition,
a pair of latching pins each of which extends outward from an opposite side of said one of said beam members at said intermediate region thereof and a lever pivoted to the other of said beam members and being pivotable from a first position at which the lever is angled relative to said other beam member and a second position at which the lever extends along said back end region of said other beam member, and
cam means for engaging said latching pins and drawing said intermediate regions of said beam members closer together and for flexing said members as said lever is pivoted from said first position to said second position to bring said front end regions of beam members into a substantially parallel relationship and to create stress forces within said beam members which resist spreading of said front end regions thereof.

18. A surgical stapler for implanting one or more rows of staples in living tissue comprising:
first and second juxtaposed beam members each having a front end region, an intermediate region and a back end region, said front end regions being spaced apart to form a tissue receiving gap therebetween, said beam members having a non-linear configuration wherein said front end regions are convergent and said back end regions are also convergent when said beam members are in an unstressed condition, one of said beam members having means for receiving at least one row of staples within said front end region thereof and firing means for sequentially forcing said staples out of said staple receiving means and into said tissue in response to translation of a first actuator element, the other of said beam member having staple tip receiving indentations shaped to close said staples as said staples penetrate through said tissue, one of said beam members having a spacer projection extending towards the other of said beam members at said front end region thereof to establish a predetermined width of said gap,
a pair of latching elements each of which extends outward from an opposite side of said one of said beam members at said intermediate region thereof and a lever pivoted to the other of said beam members and being pivotable from a first position at which the lever is angled relative to said other beam member and a second position at which the lever extends along said back end region of said other beam member, and
cam means for engaging said latching elements to draw said intermediate regions of said beam members closer together as said lever is pivoted from said first position to said second position whereby said front end regions of beam members are brought into a substantially parallel relationship and stress forces are created within said beam members that resist spreading of said front end regions thereof.

* * * * *